(12) United States Patent
Otake et al.

(10) Patent No.: US 10,130,790 B2
(45) Date of Patent: Nov. 20, 2018

(54) CATHETER AND METHOD FOR MANUFACTURING THE SAME

(71) Applicant: TERUMO KABUSHIKI KAISHA, Shibuya-ku, Tokyo (JP)

(72) Inventors: Yuya Otake, Shizuoka (JP); Kota Hamuro, Shizuoka (JP); Koichiro Tashiro, Shizuoka (JP); Mariko Maruyama, Shizuoka (JP); Tetsuya Fukuoka, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 286 days.

(21) Appl. No.: 15/003,489

(22) Filed: Jan. 21, 2016

(65) Prior Publication Data

US 2016/0136387 A1 May 19, 2016

Related U.S. Application Data

(63) Continuation of application No. PCT/JP2014/069002, filed on Jul. 17, 2014.

(30) Foreign Application Priority Data

Jul. 23, 2013 (JP) ................................. 2013-152205

(51) Int. Cl.
*A61M 25/00* (2006.01)

(52) U.S. Cl.
CPC ...... *A61M 25/005* (2013.01); *A61M 25/0012* (2013.01); *A61M 25/0045* (2013.01); *A61M 2025/006* (2013.01)

(58) Field of Classification Search
CPC .............. A61M 25/005; A61M 25/00; A61M 25/0012; A61M 2025/006;

(Continued)

(56) References Cited

U.S. PATENT DOCUMENTS

| 3,558,754 A | 1/1971 | Martin |
| 5,762,995 A | 6/1998 | Kondo et al. |

(Continued)

FOREIGN PATENT DOCUMENTS

| CN | 101085385 A | 12/2007 |
| JP | 2000-225196 A | 8/2000 |

(Continued)

OTHER PUBLICATIONS

Health Hazard Reactivity—spectrumchemical.com. (n.d.). Retrieved Nov. 8, 2016, from https://www.spectrumchemical.com/MSDS/ZQ475.pdf.*

(Continued)

*Primary Examiner* — Bradley J Osinski
*Assistant Examiner* — Nilay Shah
(74) *Attorney, Agent, or Firm* — Buchanan Ingersoll & Rooney PC (57) ABSTRACT

A catheter is disclosed which has at least a two-layered structure and can suppress decrease in function thereof by suppressing the disorder at an interface between layers during use, and a method for manufacturing the same. The catheter has an inner layer as a tube shaped body made of a thermoplastic resin and an outer layer, as a tube shaped body made of a thermoplastic resin, coming into contact with the outer surface of the inner layer, and has a reinforcement member which is at least partially embedded in the inner layer and includes a gap leading the inner layer toward the radial outside of the catheter. The inner layer has a protrusion which extends in an axial direction of the catheter while protruding from the gap to the radial outside, is positioned on the radial outside of the reinforcement member, and ingrows into the outer layer.

20 Claims, 7 Drawing Sheets

(58) Field of Classification Search
CPC .......... A61M 25/0009; A61M 25/0051; A61M 25/0052; A61M 25/0053; A61M 25/0054; F16L 11/08; F16L 11/081; F16L 11/082; F16L 11/083; F16L 11/085; B32B 1/08
See application file for complete search history.

(56) References Cited

U.S. PATENT DOCUMENTS

| | | | | |
|---|---|---|---|---|
| 5,836,926 | A | * 11/1998 | Peterson | ........... A61M 25/0012 604/264 |
| 5,938,587 | A | * 8/1999 | Taylor | ................... A61B 1/018 138/118 |
| 6,520,214 | B1 | 2/2003 | Sugiyama et al. | |
| 2005/0096567 | A1 | 5/2005 | Reynolds et al. | |

FOREIGN PATENT DOCUMENTS

| | | |
|---|---|---|
| JP | 2005-270507 A | 10/2005 |
| JP | A-2006-288670 | 10/2006 |
| JP | 2007-509713 A | 4/2007 |
| JP | 2008-229160 A | 10/2008 |
| JP | 2014-18390 A | 2/2014 |
| WO | 9732623 A1 | 9/1997 |
| WO | 02/069785 A1 | 12/2002 |

OTHER PUBLICATIONS

Nomex Polyaramid—Universita Messina (n.d.). Retrived Nov. 8, 2016, from http://ww2.unime.it/cdlchimind/adm/inviofile/uploads/HP_Pols2.b.pdf.*

International Search Report (PCT/ISA/210) dated Sep. 30, 2014, by the Japanese Patent Office as the International Searching Authority for International Application No. PCT/JP2014/069002.

Written Opinion (PCT/ISA/237) dated Sep. 30, 2014, by the Japanese Patent Office as the International Searching Authority for International Application No. PCT/JP2014/069002.

The extended European Search Report dated Jan. 2, 2017, in corresponding European Patent Office Application No. 14828772.5-1501. (7 pgs).

Office Action dated May 17, 2018 in corresponding Chinese Patent Application No. 201480038049.4, and an English translation thereof.

* cited by examiner

CATHETER AND METHOD FOR MANUFACTURING THE SAME

CROSS-REFERENCES TO RELATED APPLICATIONS

This application is a continuation of International Application No. PCT/JP2014/069002 filed on Jul. 17, 2014, which claims priority to Japanese Patent Application No. 2013-152205, filed Jul. 23, 2013, the entire contents of which are incorporated herein by reference.

TECHNICAL FIELD

The present disclosure relates to a catheter, which is inserted into a biological lumen and a method for manufacturing the same, and particularly to a guiding catheter for guiding a percutaneous transluminal coronary angioplasty (PTCA) catheter or the like to a target site and a method for manufacturing the same.

BACKGROUND DISCUSSION

The guiding catheter is a catheter, which guides a PTCA catheter or the like for treating the coronary arteries of the heart when inserting the PTCA catheter or the like to a target site.

A guiding catheter with a smaller outer diameter is expected in order to reduce the burden on a patient (specifically to reduce the size of an incision of an insertion portion of a blood vessel and to reduce friction between the guiding catheter and the blood vessel). In contrast, a PTCA catheter which is used for treatment and is a larger size is expected in order to exhibit a sufficient effect in a treatment site. For this reason, a guiding catheter with a larger inner diameter is expected.

In recent years, a guiding catheter having an outer diameter of, for example, 6 Fr (2.06 mm) or 7 Fr (2.36 mm) has mainly been used. A guiding catheter with a smaller outer diameter is less invasive with respect to a patient, but the procedure becomes relatively difficult. In addition, if the wall thickness of a guiding catheter is made thin while maintaining the outer diameter of the guiding catheter to be fixed, the tube wall naturally becomes weak and crushing or breakage (kinking) can be easily caused.

In addition, kink resistance improves as a catheter shaft portion of a guiding catheter or the like is flexible, but high pushability (transmission performance of pushing force) or high torque transmission performance is not obtained while inserting the guiding catheter into a blood vessel. For this reason, it is difficult for the catheter having a flexible catheter shaft portion to pass a meandering blood vessel. In addition, in a case where a distal portion of a catheter has a curved shape, if the section provided with the curved shape in the distal portion is too soft, a distal end of the catheter can be easily deviated from a coronary artery hole due to an operation, such as insertion of a PTCA catheter or the like, of a device after the distal end of the catheter is engaged with the coronary artery hole through the aorta.

For this reason, as a catheter which has a small outer diameter and has high pushability and high kink resistance, a catheter which is provided with a reinforcement layer formed of a plurality of reinforcement wires between an inner layer and an outer layer is disclosed in JP-A-2006-288670.

In the above-described catheter disclosed in JP-A-2006-288670, a mesh-like reinforcement layer is provided between the inner layer and the outer layer. Therefore, the area on which the inner layer and the outer layer come into contact with each other is narrow, and thus, bonding strength between the inner layer and the outer layer is not relatively high. For this reason, structure disorder such as separation at an interface between the inner layer and the outer layer can occur relatively easily due to application of flexural stress, torsional stress, or the like during use of the catheter, and therefore, the physical properties of the catheter easily change. When the physical properties of the catheter change, the flexibility of the catheter can deteriorate, and therefore, kinking may easily occur in the middle of use, or the performance such as pushability or torque transmission performance can deteriorate.

SUMMARY

A catheter is disclosed which has at least a two-layered structure and can suppress the change in performance such as flexibility or the like by suppressing the structure disorder at an interface between layers as much as possible when in use, and a method for manufacturing the same.

A catheter according to the present disclosure for achieving the aforesaid purpose has an inner layer as a tube shaped body made of a thermoplastic resin and an outer layer, as a tube shaped body made of a thermoplastic resin, coming into contact with the outer surface of the inner layer. The catheter has a reinforcement member, which is at least partially embedded in the inner layer and can include a gap leading the inner layer toward the radial outside of the catheter. The inner layer has a protrusion, which extends in an axial direction of the catheter while protruding from the gap to the radial outside, is positioned on the radial outside of the reinforcement member, and ingrows into the outer layer.

In the catheter constituted as described above, the protrusions of the inner layer extend to a position at which the protrusions overlap the reinforcement member radially outward, in the axial direction and ingrow into the outer layer. Accordingly, the contact area between the inner layer and the outer layer becomes large, and therefore, the bonding strength between the inner layer and the outer layer increases. For this reason, even if the flexural stress, the torsional stress, or the like is applied to the catheter during use of the catheter, the change in the performance of the catheter can be suppressed by suppressing the structure disorder at an interface between the inner layer and the outer layer.

In accordance with an exemplary embodiment, if the plurality of protrusions protruding from the different gaps are made to overlap each other in multiple layers toward the radial outside of the reinforcement member while interposing the outer layer, the contact area between the inner layer and the outer layer becomes large and the bonding strength between the inner layer and the outer layer further increases. Thus, the change in the performance of the catheter can be suppressed by suppressing the structure disorder at the interface between the inner layer and the outer layer.

In accordance with an exemplary embodiment, if the reinforcement member is made to be formed of a wire made of resin having a higher melting point than that of the inner layer, or of metal, which is interposed between the inner layer and the outer layer, the bonding strength between the inner layer and the outer layer can be increased using the reinforcement member which becomes a factor for reducing the contact area between the inner layer and the outer layer, without providing a separate structure.

In accordance with an exemplary embodiment, if the gaps of the reinforcement member are made to be formed by being divided in the circumferential direction of the inner layer, the protrusions portions which are formed using the gaps are formed by being divided in the circumferential direction. Therefore, the bonding strength between the inner layer and the outer layer can be increased by increasing the contact area between the inner layer and the outer layer. Furthermore, even if the structure disorder occurs at an interface between the inner layer and the outer layer, the protrusions portions are formed by being divided in the circumferential direction. Therefore, the progress of the disorder in the circumferential direction can be suppressed and high bonding strength can be maintained.

In accordance with an exemplary embodiment, if the inner layer and the outer layer are made to be formed of the same kinds of thermoplastic resins, the compatibility of the inner layer and the outer layer becomes high, and therefore, the bonding strength can be increased at an interface therebetween. Note that the compatibility means mutual solubility between different kinds of molecules. Here, the compatibility means easiness of being mixed in a molecular level of the thermoplastic resin of the inner layer and the thermoplastic resin of the outer layer which are formed separately from each other.

In addition, with a method for manufacturing a catheter which has an inner layer as a tube shaped body made of a thermoplastic resin and an outer layer, as a tube shaped body made of a thermoplastic resin, coming into contact with the outer surface of the inner layer, the method can include an intermediate step of disposing a reinforcement member having gaps on the outer surface of an inner layer tube which is the tube shaped body made of a thermoplastic resin while embedding the reinforcement member in the outer surface thereof, and forming an intermediate structure by making the material of the inner layer tube protrude radially outward from the gap; and an arrangement step of disposing a material for the outer layer, which is made of a thermoplastic resin, on the outer surface of the intermediate structure, in which, in the arrangement step, the inner layer and the outer layer are formed by bonding the inner layer tube and the material for the outer layer to each other while fluidizing the inner layer tube and the material for the outer layer in a state in which the inner layer tube and the material for the outer layer have fluidity, the material of the inner layer protruding from the gap of the reinforcement member is moved while being fluidized in the arrangement step, and therefore, the bonding strength between the inner layer and the outer layer can be increased.

In the arrangement step, if the inner layer and the outer layer are made to be formed by applying force to the outer surface of the material for the outer layer toward the direction facing the intermediate structure or the axial direction of the intermediate structure in a state in which the inner layer tube and the material for the outer layer have fluidity, and by bonding the inner layer tube and the material for the outer layer to each other while fluidizing the inner layer tube and the material for the outer layer, the inner layer which is provided with the protrusions extending in the axial direction while protruding from each of the gaps of the reinforcement member radially outward can be formed relatively easily.

In the intermediate step, if at least either of the inner layer tube and the reinforcement member is made to be heated, it becomes relatively easy to partially embed the reinforcement member having the gaps in the outer surface of the inner layer tube.

In accordance with an exemplary embodiment, if the inner layer tube is heated in the arrangement step, the inner layer tube can be provided with fluidity in a case where the inner layer tube does not have the fluidity before the bonding step.

In the arrangement step, if the fluidities of the material of the inner layer tube and the material for the outer layer are made to be different from each other, it becomes relatively easy to form the inner layer and the outer layer in a layered shape.

DETAILED DESCRIPTION

Hereinafter, an embodiment of the present disclosure will be described while referring to the drawings. Note that, in some cases, the dimensional ratios in the drawings are exaggerated and are different from the actual ratios for the convenience of description.

Note that, in the description below, the hand side of a catheter is referred to as a "proximal side" and the side into which the catheter is inserted is referred to as a "distal side". In addition, the "catheter" represents a catheter including a tube body, which is used for a medical purpose. The application of the catheter is not limited to the medical purpose, and may be used for, for example, an examination.

Figure 1:
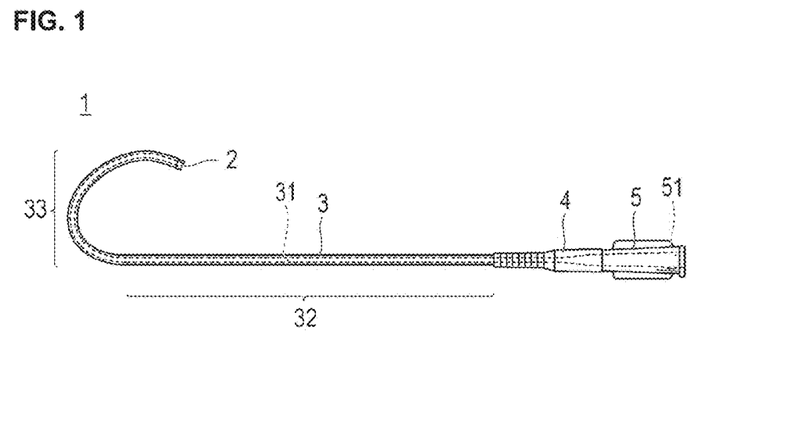
FIG. 1 is a plan view showing a catheter according to an exemplary embodiment of the present disclosure.

A catheter 1 according to the present exemplary embodiment shown in FIG. 1 can be used as a guiding catheter for deriving a treatment device, for example, a dilation catheter (balloon catheter) for PTCA or a catheter (stent delivery catheter) for delivering a stent to a stenosed site in a state in which the diameter of the stent is reduced, and for expanding the stenosed site and maintaining the expansion thereof by indwelling the stent in the stenosed site after increasing the diameter of the stent, to a target site such as a stenosed site of the coronary arteries.

The catheter 1 is constituted of a catheter main body 3; a soft tip 2 which is provided on a distal side of the catheter main body 3 and is highly flexible; and a hub 5 which is provided on a proximal side of the catheter main body 3. In addition, a strain relief an anti-kink protector 4 formed of an elastic material is provided in a section in which the catheter main body 3 and the hub 5 are connected to each other. Accordingly, bending (kinking) in the vicinity of the section in which the catheter main body 3 and the hub 5 are connected to each other can be prevented.

The catheter main body 3 is constituted of a flexible tube shaped body, and a lumen 31 which penetrates the catheter main body 3 over the full length thereof is formed inside the catheter main body 3. The lumen 31 is open at a distal end of the soft tip 2.

Figure 2:
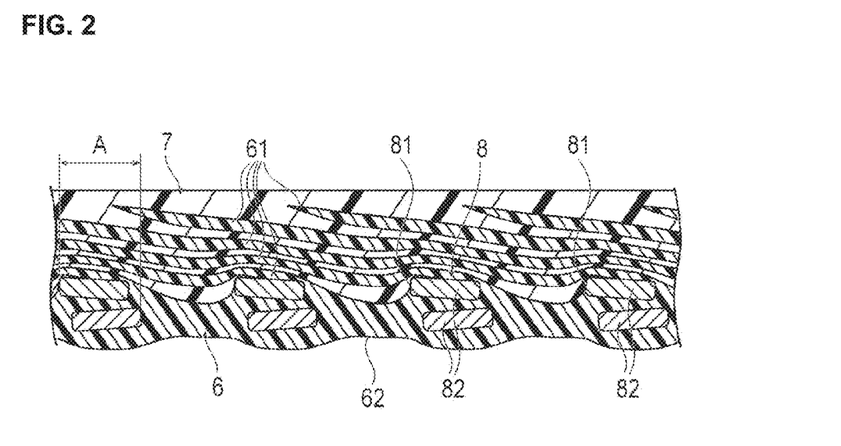
FIG. 2 is a partial longitudinal sectional view of the catheter according to the exemplary embodiment of the present disclosure.

The tube shaped body constituting the catheter main body 3 has, as shown in FIG. 2, an inner layer 6 constituting the inner surface of the tube shaped body; an outer layer 7 constituting the outer surface of the tube shaped body; and a reinforcement member 8 which is positioned between the inner layer 6 and the outer layer 7 and is provided with a plurality of gaps 81 so as to partially cover the outer surface of the inner layer 6.

Figure 3:
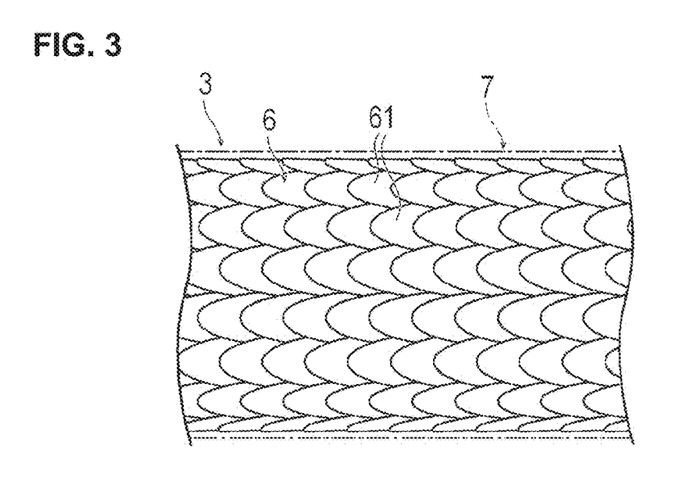
FIG. 3 is a transparent view in which only an inner layer is observed through an outer layer and a reinforcement member of the catheter according to the exemplary embodiment of the present disclosure.

As shown in FIG. 3, in which only the inner layer 6 is observed through the outer layer 7 and the reinforcement member 8, and in FIG. 2, the inner layer 6 includes a plurality of protrusions 61 protruding radially outward from each of the gaps 81 of the reinforcement member 8. The protrusions 61 protrude radially outward so as to ingrow into the outer layer 7 and are formed extending to a distal side in an axial direction up to a position (refer to a range A in FIG. 2) at which the protrusions overlap the reinforcement member 8 radially outward. Note that the direction in which the reinforcement member 8 extends may be a proximal side in the axial direction. With the formation of the protrusions 61 from each of the gaps 81 which are formed in a mesh shape by being divided in a circumferential direction, the protrusions 61 overlap each other and are arranged in the circumferential direction and the axial direction, and are disposed in a scale-like shape.

The plurality of protrusions 61 protruding from different gaps 81 overlap each other in multiple layers toward the radial outside of a linear body 82 constituting the reinforcement member 8 while interposing the outer layer 7. Note that, in the present exemplary embodiment, four to five protrusions 61 are stacked on each other on the radial outside of the reinforcement member 8 while interposing the outer layer 7 (refer to the range A in FIG. 2), but the number of the protrusions stacked on each other is not limited thereto as long as the number of the protrusions stacked on each other is greater than or equal to one.

As described above, the protrusions 61 of the inner layer 6 extend in the axial direction up to the position, at which the protrusions overlap the reinforcement member 8 radially outward, and ingrow into the outer layer 7. Therefore, the bonding strength between the inner layer 6 and the outer layer 7 increases. Furthermore, since the inner layer 6 and the outer layer 7 complicatedly come into contact with each other so as to overlap each other, the contact area between the inner layer 6 and the outer layer 7 is large, which also becomes a cause of increasing the bonding strength between the inner layer 6 and the outer layer 7. Accordingly, even if flexural stress, torsional stress, or the like is applied to the catheter 1 during use of the catheter 1, structure disorder such as separation at an interface between the inner layer 6 and the outer layer 7 or the like hardly occurs. Therefore, the physical property such as the flexural rigidity, torsional rigidity or the like of the catheter 1 hardly deteriorates. For this reason, the flexibility of the catheter 1 can be maintained and the kink resistance or the performance such as high pushability, high torque transmission performance or the like when in use for a long period of time can be favorably maintained.

The constituent materials of both of the inner layer 6 and the outer layer 7 can be thermoplastic resins, and examples of the thermoplastic resins can include nylon, polyester, polyamide, polyurethane, polyolefin, thermoplastic fluororesin and the like. The constituent materials of the inner layer 6 and the outer layer 7 are preferably the same kinds. Note that the same kinds in the present specification means that the inner layer and the outer layer have a repeating unit of the same functional group as each other. For example, nylon and nylon elastomer have a repeating unit of the same functional group as each other, and therefore, are of the same kinds. High compatibility can be obtained if the constituent materials of the inner layer 6 and the outer layer 7 are the same kinds of resins. Therefore, the bonding strength of the interface becomes relatively high, the structure disorder hardly occurs, and a reduction in the performance can be suppressed.

Regarding the constituent materials of the inner layer 6 and the outer layer 7, it is preferable that the fluidities of the materials are different from each other at a temperature when stacking the outer layer 7. With the provision of the different fluidities, the inner layer 6 and the outer layer 7 easily become layered shapes.

Examples of the method of differentiating the fluidities of the inner layer 6 and the outer layer 7 can include a method of using materials having different melting points or materials having different resin viscosities, for the inner layer 6 and the outer layer 7. For example, the constituent material of the inner layer 6 is nylon elastomer and the constituent material of the outer layer 7 is nylon. Even if the materials of the inner layer 6 and the outer layer 7 are the same as each other, it is possible to change differentiate the fluidities thereof from each other in accordance with the molding conditions or the like (for example, one material being made to be easily heated).

In accordance with an exemplary embodiment, the constituent material of the inner layer 6 is preferably formed of a material in which at least a section coming into contact with devices such as treatment catheter, a guide wire and the like which are not shown in the drawing has low friction when inserting these devices into the lumen 31 of the catheter main body 2. Accordingly, the devices which have been inserted into the catheter main body 3 can be moved in a longitudinal direction with smaller sliding resistance, thereby contributing to the improvement of the operability. Examples of the constituent material with low friction include polyolefin and thermoplastic fluororesin, out of the above-described thermoplastic resins.

In addition, projections and recesses for reducing the contact area between an inner surface 62 and a treatment device may be formed on the inner surface of the inner layer 6. The projections and recesses can be formed relatively easily using a phenomenon in which the material of the inner layer 6 flows so as to be dragged radially outward in a bonding step of a manufacturing method to be described below. Alternately, the projections and recesses may be formed on the inner surface 62 of the inner layer 6 which is formed on a core wire, by forming a concave portion or a convex portion on the outer surface of the core wire which is disposed inside the inner layer 6 during the manufacturing.

Figure 4:
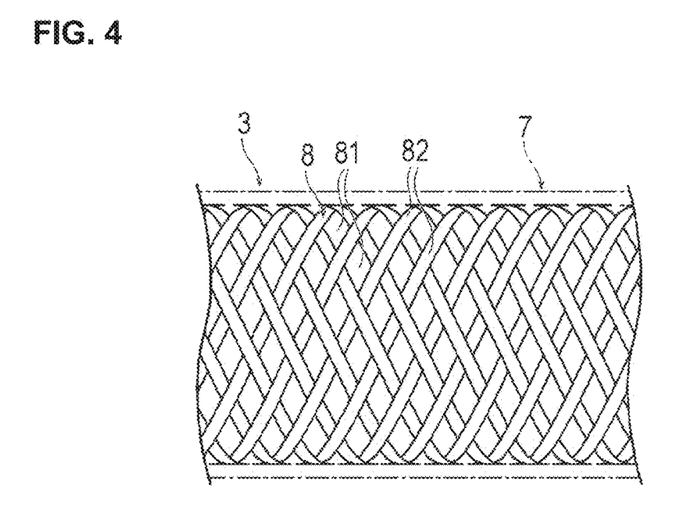
FIG. 4 is a transparent view in which only a reinforcement member is observed through an inner layer and the outer layer of the catheter according to the exemplary embodiment of the present disclosure.

As shown in FIG. 4 in which only the reinforcement member 8 is observed through the inner layer 6 and the outer layer 7, and in FIG. 2, the gaps 81 can be formed in the reinforcement member so as to guide the protrusions 61 of the inner layer 6 radially outwardly, and therefore, the reinforcement member 8 is partially embedded in the inner layer 6 without being completely embedded in the inner layer. Accordingly, the reinforcement member 8 comes into contact with both of the inner layer 6 and the outer layer 7.

In accordance with an exemplary embodiment, the reinforcement member 8 can have a plurality of linear bodies 82 reinforcing the catheter main body 3. In the present exemplary embodiment, the reinforcement member 8 is formed in a mesh shape using the plurality of linear bodies 82, and the gaps 81 are formed in lattice shapes. Note that, in the reinforcement member 8, the linear bodies 82 are not limited to being formed in the mesh shape. For example, the linear bodies may be made to be a spiral shape or a plurality of window-like gaps (opening portions) may be formed on one tube shaped body. The shapes of the protrusions 61 of the inner layer 6 vary depending on the shapes of the gaps 81. For example, if the gaps are in a spiral shape, the protrusions are formed in the spiral shape so as to be continuously stretched in a circumferential direction.

As the constituent material of the linear body 82, for example, metallic materials such as stainless steel, copper, tungsten, boron, shape memory/superelastic alloy (NiTi) and the like; inorganic fiber materials such as alumina fibers, silicon carbide fibers, carbon fibers and the like; and organic fiber materials such as nylon, polyester, polyethylene, engineering plastics, liquid crystal polymers and the like can be applied. In a case where the constituent material of the linear body 82 is resin, the melting point of the constituent material of the linear body 82 is higher than those of the inner layer and the outer layer.

A linear body which is obtained by, for example, subjecting a stainless steel wire to crushing processing so as to become a flat plate to reduce the wall thickness of the catheter main body 3 in the radial direction can be used as the linear body 82. With such a reinforcement member 8, sufficient rigidity and strength can be secured while relatively increasing the inner diameter (diameter of the lumen 31) without increasing the wall thickness of the catheter main body 3. As a result, the catheter 1 can be obtained through which a treatment catheter with a relatively large outer diameter can be inserted, which is excellent in pushability and torque transmission performance, and in which kinking and crushing hardly occur.

Note that the number of layers constituting the catheter main body 3, the constituent materials of each layer, the presence and absence of a reinforcement material, and the like may vary depending on sections along the longitudinal direction of the catheter main body 3. For example, in order to make the section on the distal side of the catheter main body 3 have more flexibility, the number of layers can be reduced, more flexible material can be used, or the reinforcement material may not be disposed only in the section.

Such a catheter main body 3 has, as shown in FIG. 1, a straight portion 32 which extends almost in a straight shape from the proximal side; and a curved portion 33 which further extends toward the distal end from the straight portion 32 and forms a desired curved shape, in a longitudinal direction. The curved portion 33 is curved in a shape suitable for a site of the left coronary artery, the right coronary artery, or the like through which the curved portion is inserted. For example, the curved portion 33 forms a shape so as to facilitate an operation (engagement operation) of being engaged with an opening of the coronary artery, or a shape so as to more reliably maintain the state (engagement) of being engaged with the opening of the coronary artery.

The soft tip 2 can be formed of a highly flexible material and a distal end of the soft tip preferably forms a round shape. With the provision of such a soft tip 2, it is possible to make the soft tip travel smoothly and safely even within a blood vessel which has been curved, bent, and branched. Examples of the constituent material of the soft tip 2 can include various rubber materials such as natural rubber, isoprene rubber, butadiene rubber, chloroprene rubber, silicone rubber, fluorine rubber, styrene-butadiene rubber, and the like; and various thermoplastic elastomers based on styrene, polyolefin, polyurethane, polyester, polyamide, polybutadiene, trans-polyisoprene, fluororubber, chlorinated polyethylene, and the like.

The length of the soft tip 2 is not particularly limited, but in general, is preferably, for example, about 0.5 mm to 3 mm and more preferably, for example, about 1 mm to 2 mm.

The insertion of the catheter 1 into the body is performed while checking the position of the catheter under X-ray radioscopy. Therefore, it can be preferable that a radiopaque material (X-ray contrast agent) is blended with the soft tip 2 which is positioned at the distal end of the catheter 1 or with an end portion of the linear body 82. As the radiopaque material, for example, barium sulfate, bismuth oxide, or tungsten can be used. The proportion at which the radiopaque material is blended is preferably, for example, 30 wt % to 80 wt %.

In addition, such a radiopaque material may be present over the full length of the catheter main body 3. Such a radiopaque material may be present in, for example, the outer layer 7 or the inner layer 6.

The hub 5 is installed at the proximal end of the catheter main body 3. A passage 51 which communicates with the lumen 31 is formed in this hub 5. This passage 51 is continuous to the inner surface of the proximal portion of the lumen 31 without creating a step or the like.

It is possible to perform, for example, insertion or removal of an elongated subject, such as a guide wire, catheters (for example, a PTCA balloon catheter, a stent delivery catheter), an endoscope, an ultrasound probe, a temperature sensor or the like, or to perform injection of various liquids, such as a contrast agent (X-ray contrast agent), a drug solution, a saline physiological salt solution and the like, through such a hub 5. In addition, the hub 5 can be, for example, connected to other instruments such as a Y-shaped connector or the like.

Next, a method for manufacturing the catheter 1 according to the present embodiment will be described.

Figure 5:
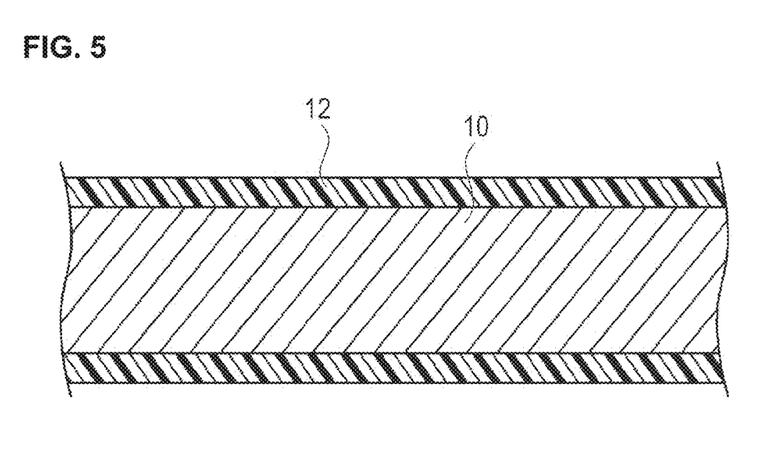
FIG. 5 is a longitudinal sectional view showing a state in which an inner layer tube is molded on a core wire.

First, a core wire 10 is prepared, and as shown in FIG. 5, an inner layer tube 12 before becoming the inner layer 6 is extrusion-molded on the core wire 10. Note that the inner layer tube 12 may be molded through a different method than that of the extrusion molding.

Figure 6:
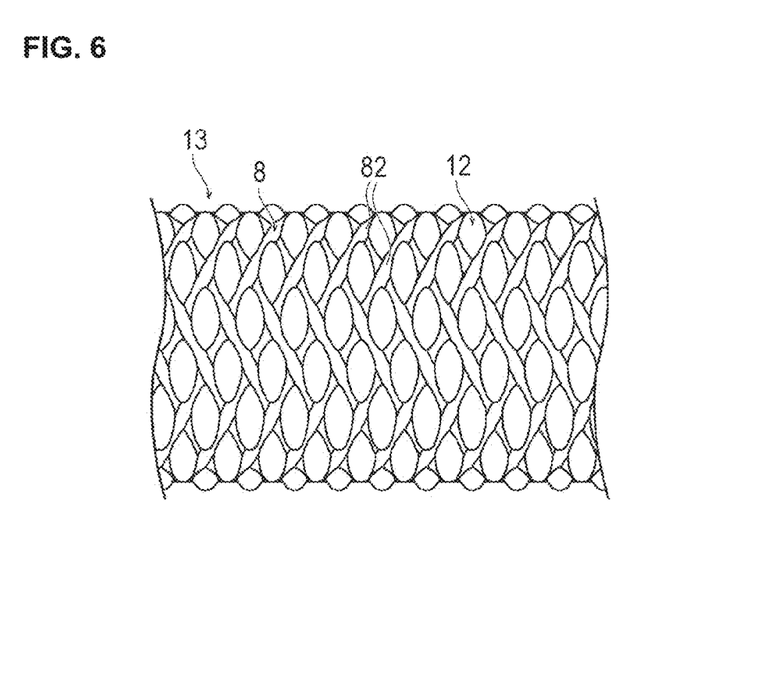
FIG. 6 is a plan view showing an intermediate structure in which the inner layer tube is covered with the reinforcement member.
Figure 7:
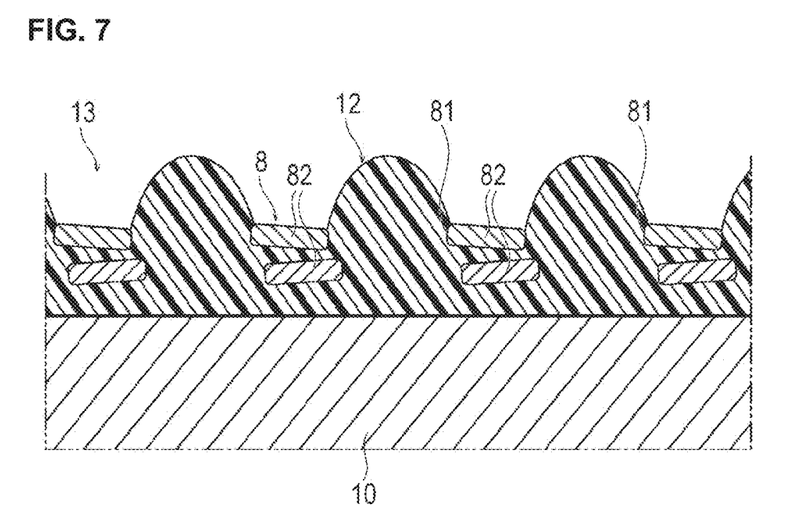
FIG. 7 is a longitudinal sectional view showing the intermediate structure in which the inner layer tube is covered with the reinforcement member.

Next, the linear body 82 is braided using a braider to form the reinforcement member 8 on the outer surface of the inner layer tube 12. When braiding the linear body 82, the reinforcement member 8 is partially embedded in the inner layer tube 12 as shown in FIGS. 6 and 7 by heating at least either of the inner layer tube 12 and the linear body 82, to form an intermediate structure 13 in which the material of the inner layer tube 12 protrudes radially outward from the gap 81 of the reinforcement member 8 (intermediate step).

Alternately, the intermediate structure 13 can be formed in which the material of the inner layer tube 12 protrudes radially outward from the gap 81 of the reinforcement member 8, by braiding the linear body 82 in the inner layer tube 12 immediately after being extruded by an extruder and before being solidified.

Figure 8:
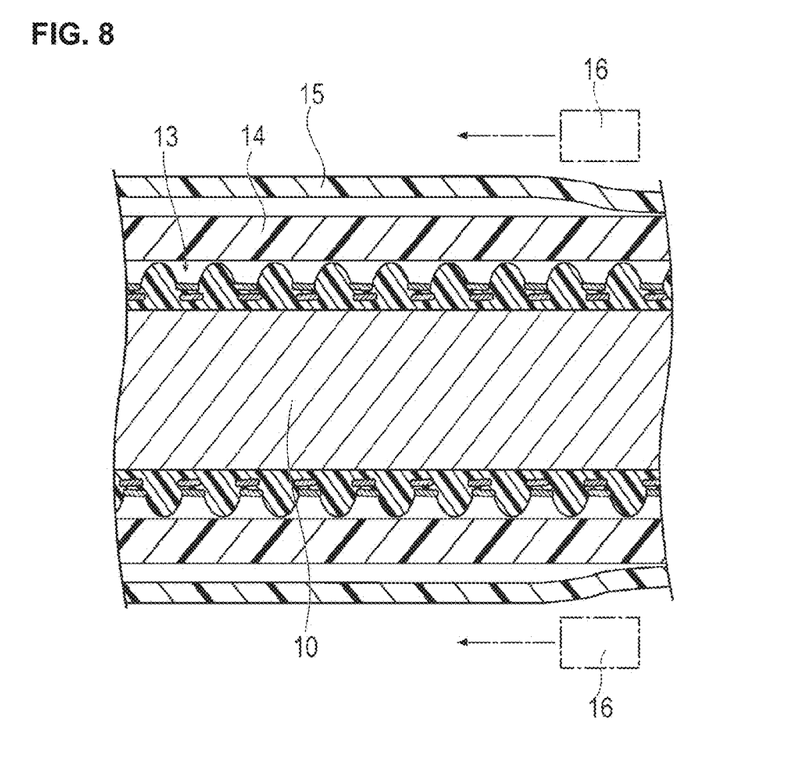
FIG. 8 is a longitudinal sectional view showing a state when the intermediate structure is covered with the outer layer.

Next, as shown in FIG. 8, the intermediate structure 13 is covered with an outer layer tube 14 (material for an outer layer) which is a tube shaped body before becoming the outer layer 7, and the outside of the outer layer tube is further covered with a heat shrinkable tube 15, which is then heated using a heat source 16 such as a heater or the like from one end side, and the heat source 16 is gradually moved to the other end. The temperature of the heat source 16 is a temperature at which both of the inner layer 6 and the outer layer 7 are softened so as to have fluidity. Note that the intermediate structure 13, the outer layer tube 14, and the heat shrinkable tube 15 may be moved to the heat source 16 without moving the heat source 16. Accordingly, the fluidity can be provided to the outer layer tube 14 and the inner layer tube 12 by being softened, and the outer layer tube 14 is pressed to the inner layer tube 12 by the heat shrinkable tube 15. Furthermore, since the heat source 16 moves relative to the intermediate structure 13, the outer layer tube 14, and the heat shrinkable tube 15, the shrinkage position of the heat shrinkable tube 15 gradually moves. Moreover, the materials of the softened outer layer tube 14 and inner layer tube 12 which have obtained fluidity move toward the relative movement direction of the heat source 16, that is, toward a side opposite to the movement direction of the intermediate structure 13, while being stretched so as to be extruded, so as to form the inner layer 6 and the outer layer 7 while the inner layer and the outer layer are bonded to each other (arrangement step). At this time, in the heated intermediate structure 13, the material of the inner layer tube 12 protrudes from the gap 81 of the reinforcement member 8, and therefore, the inner layer 6 provided with the protrusions 61 extending in the axial direction while protruding radially outward from each of the gaps 81 of the reinforcement member 8 is formed through the stretching of the material of the inner layer tube 12 protruding from the gap 81.

Note that, as the covering method of the outer layer 7, an extrusion molding method may be used without using the heat shrinkable tube 15. In order to mold the outer layer 7 through extrusion molding, the fluidity is provided to the inner layer tube 12 by heating the intermediate structure 13, and the outer surface is covered with an outer layer tube (material for the outer layer) in a state of having fluidity before becoming the outer layer 7 made of a thermoplastic resin through the extrusion molding. Note that it is unnecessary to heat the inner layer tube 12 again in a case where the inner layer tube 12 does not lose the fluidity immediately after being molded. Thereafter, the extruded outer layer tube passes through an annular die defining the outer surface of the outer layer 7, the materials of the outer layer tube and the inner layer tube 12 which have fluidity move toward a side opposite to the movement direction of the intermediate structure 13, while being stretched so as to be extruded, so as to form the inner layer 6 and the outer layer 7 while the inner layer and the outer layer are bonded to each other (arrangement bonding step). At this time, the inner layer 6 provided with the protrusions 61 extending in the axial direction while protruding radially outward from each of the gaps 81 of the reinforcement member 8 is formed as shown in FIG. 2 through the stretching of the material of the inner layer tube 12 protruding from the gap 81 of the reinforcement member 8.

Next, the core wire 10 is pulled out, unnecessary sites on both ends thereof are cut off, and other types of processing are performed if necessary to complete the production of the catheter main body 3. Thereafter, the catheter main body 3 and the soft tip 2 are welded by disposing a tube shaped body which becomes the soft tip 2 at the distal end of the catheter main body 3 and covering the tube shaped body with a heat shrinkable tube for heating. Alternately, the soft tip 2 may be molded at the distal end of the catheter main body 3 through the extrusion molding.

Thereafter, the hub 5 and the strain relief anti-kink protector 4 are attached thereto to complete the manufacturing of the catheter 1.

As described above, in the catheter 1 according to the present embodiment, the protrusions 61 of the inner layer 6 extend to a position at which the protrusions overlap the reinforcement member 8 radially outward, in the axial direction and ingrow into the outer layer 7. Accordingly, the contact area between the inner layer and the outer layer becomes relatively large, and therefore, the bonding strength between the inner layer 6 and the outer layer 7 increases. For this reason, even if the flexural stress, the torsional stress, or the like is applied to the catheter 1 during use of the catheter 1, the deterioration of (change in) the performance can be suppressed, such as kink resistance, high pushability, high torque transmission performance or the like, of the catheter 1 by suppressing the occurrence of the structure disorder at an interface between the inner layer 6 and the outer layer 7 as much as possible.

In addition, the plurality of protrusions 61 protruding from the different gaps 81 overlap each other in multiple layers toward the radial outside of the reinforcement member 8 while interposing the outer layer 7. Therefore, the contact area between the inner layer 6 and the outer layer 7 becomes wider and the bonding strength between the inner layer 6 and the outer layer 7 increases. Thus, the deterioration of (change in) the performance of the catheter 1 can be further suppressed by suppressing the occurrence of the structure disorder at the interface between the inner layer 6 and the outer layer 7.

In addition, the reinforcement member 8 interposed between the inner layer 6 and the outer layer 7 is formed of a wire made of resin, which has a higher melting point than that of the inner layer, or of metal. Therefore, the bonding strength between the inner layer 6 and the outer layer 7 can be increased by using the reinforcement member 8 which becomes a factor for reducing the contact area between the inner layer 6 and the outer layer 7, without providing a separate structure.

In addition, since the gaps 81 of the reinforcement member 8 are formed by being divided in the circumferential direction of the inner layer 6, the protrusions 61 which are formed using the gaps 81 are formed by being divided in the circumferential direction. Therefore, the bonding strength between the inner layer 6 and the outer layer 7 can be increased by increasing the contact area between the inner layer 6 and the outer layer 7. Furthermore, even if the structure disorder occurs at an interface between the inner layer 6 and the outer layer 7, the protrusions 61 are formed by being divided in the circumferential direction. Therefore, the progress of the disorder in the circumferential direction can be suppressed and high bonding strength can be maintained.

In addition, if the inner layer 6 and the outer layer 7 are made to be formed of the same kinds of thermoplastic resins, the compatibility of the inner layer 6 and the outer layer 7 becomes high, and therefore, the bonding strength at an interface therebetween can be increased.

In addition, a method for manufacturing the catheter 1 according to the present embodiment can include an intermediate step of disposing the reinforcement member 8 having the gaps 81 on the outer surface of the inner layer tube 12 which is a tube shaped body made of a thermoplastic resin while embedding the reinforcement member in the outer surface thereof, and forming the intermediate structure 13 by making the material of the inner layer tube 12 protrude from a gap 81 to the radial outside of the catheter 1; and an arrangement step of disposing the outer layer tube 14 (material for an outer layer), which is a tube shaped body made of a thermoplastic resin, on the outer surface of the intermediate structure 13. In the arrangement step, the outer layer 76 and the inner layer 67 are formed while fluidizing the inner layer tube 12 and the outer layer tube 14 in a state in which the inner layer tube 12 and the outer layer tube 14 have fluidity. For this reason, in the arrangement step, the material of the inner layer tube 12 protruding from the gap 81 of the reinforcement member 8 moves toward the axial direction of the catheter 1, and therefore, it is possible to easily form the inner layer 6 which is provided with the protrusions 61 extending in the axial direction while protruding from each of the gaps 81 of the reinforcement member 8 radially outward.

In addition, in the arrangement step, the inner layer 67 and the outer layer 76 are formed by applying force to the outer surface of the material of the outer layer tube 14 toward the direction facing the intermediate structure 13 or the axial direction of the intermediate structure 13 in a state in which the inner layer tube 12 and the outer layer tube 14 (material for an outer layer) have fluidity, and by bonding the inner layer tube 12 and the outer layer tube 14 to each other while fluidizing the inner layer tube and the outer layer tube. Therefore, the material of the inner layer tube 12 protruding from a gap 81 of the reinforcement member 8 moves to the axial direction of the catheter 1 while being stretched, and therefore, it is possible to easily form the inner layer 6 which is provided with the protrusions 61 extending in the axial direction while protruding radially outward from each of the gaps 81 of the reinforcement member 8.

In addition, in the intermediate step, at least either of the inner layer tube 12 and the reinforcement member 8 is heated. Therefore, it becomes relatively easy to partially embed the reinforcement member 8 having the gaps 81 in the outer surface of the inner layer tube 12.

In addition, the inner layer tube 12 is heated before the arrangement bonding step. Therefore, it is possible to provide the inner layer tube 12 with fluidity in a case where the inner layer tube 12 does not have the fluidity before the bonding step.

In addition, in an arrangement joining step, the fluidities of the materials of the inner layer tube 12 and the outer layer tube 14 are different from each other, and therefore, it becomes relatively easy to form the inner layer 6 and the outer layer 7 in a layered shape.

Hereinafter, examples of the present disclosure will be described.

The material of an inner layer was set to polyester elastomer with Shore D68 and the material of an outer layer was set to polyester elastomer with Shore D52. An inner layer tube was produced through extrusion molding of polyester elastomer with Shore D68, which was the material of the inner layer, on a core wire. Next, stainless steel plane reinforcement wires (wire shaped bodies) (a set of 16 bodies) with a width of 110 μm and a thickness of 35 μm were wound on the outer surface of the inner layer tube by being braided at intervals of 0.2 mm while heating the wires, to obtain an intermediate structure.

Thereafter, the intermediate structure was covered with an outer layer tube which was the material of the outer layer and was produced to have Shore D52 and the outside thereof was covered with a heat shrinkable tube, which was then heated using a heat source from one end side, and the heat source was gradually moved to the other end side to bond the inner layer tube and the outer layer tube to each other. Then, the core wire was pulled out to produce a catheter main body. Accordingly, the catheter main body which has a penetrated lumen and has an outer diameter of 2.06 mm, an inner diameter of 1.80 mm, and an inner/outer diameter ratio of 0.87 was obtained.

Figure 9:
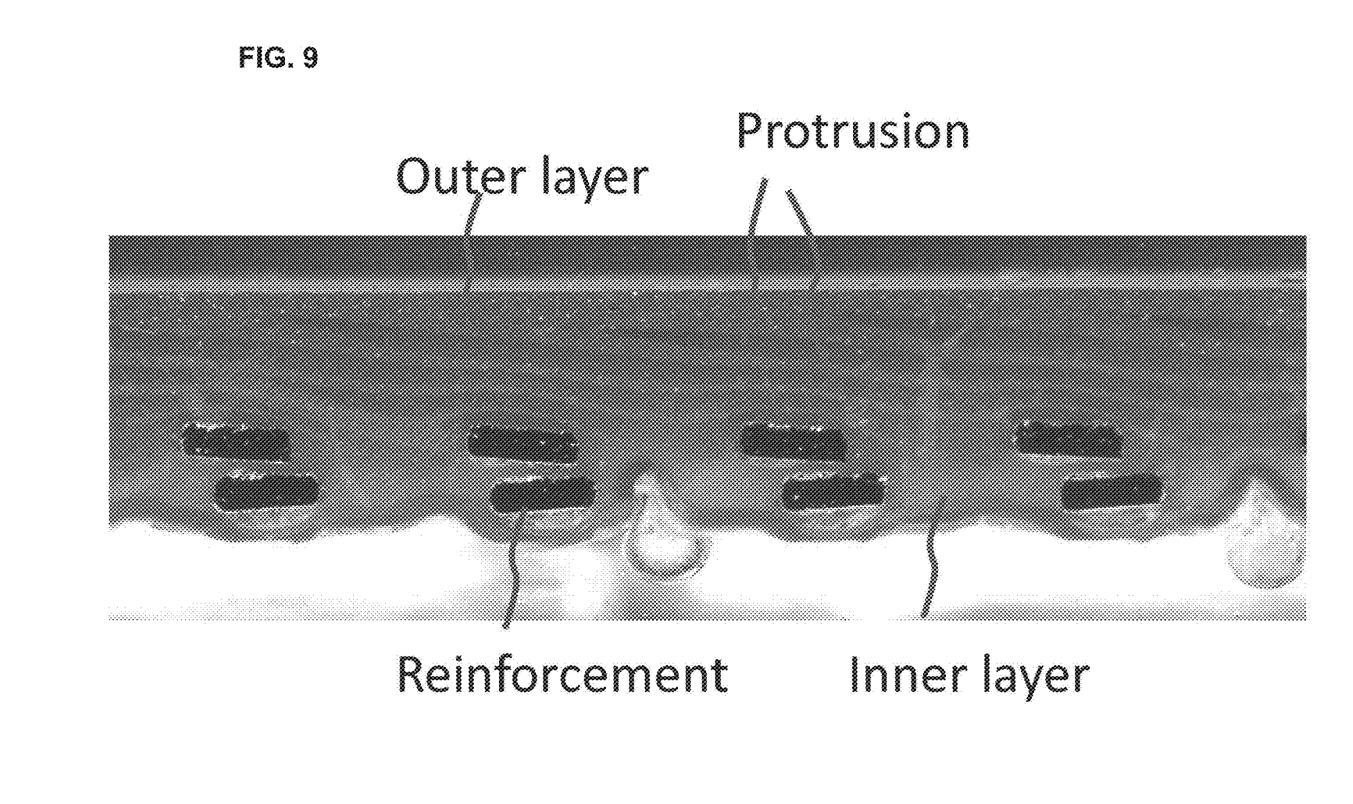
FIG. 9 is a photograph of a longitudinal cross section of a catheter main body of Example 1, which is cut along an axial direction.

Thereafter, a part of the manufactured catheter main body was cut along an axial direction and the longitudinal cross section was observed. FIG. 9 shows a photograph of a photograph which was obtained by photographing the longitudinal cross section of the catheter main body of Example 1. As shown in FIG. 9, it was confirmed that four to five protrusions were stacked on each other on the radial outside of each reinforcement wire constituting a reinforcement member while interposing the outer layer.

The material of an inner layer was set to polyester elastomer with Shore D78 and the material of an outer layer was set to polyester elastomer with Shore D52. A catheter main body was manufactured while maintaining other conditions the same as those in Example 1. Accordingly, the catheter main body which has a penetrated lumen and has an outer diameter of 2.06 mm, an inner diameter of 1.80 mm, and an inner/outer diameter ratio of 0.87 was obtained.

Figure 10:
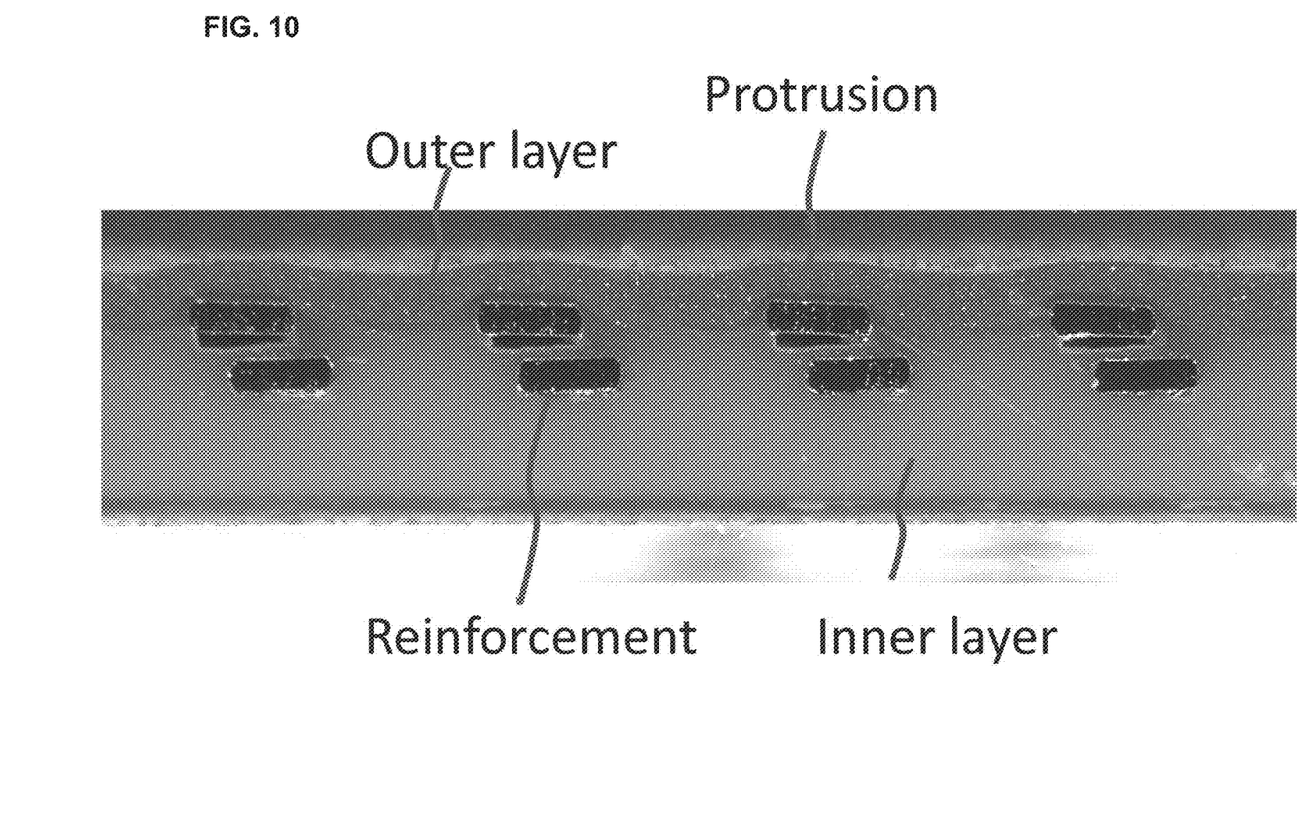
FIG. 10 is a photograph of a longitudinal cross section of a catheter main body of Example 2, which is cut along an axial direction.

Thereafter, a part of the manufactured catheter main body was cut along an axial direction and the cross section was observed. FIG. 10 shows a photograph of a photograph which was obtained by photographing the longitudinal cross section of the catheter main body of Example 2. As shown in FIG. 10, it was confirmed that one protrusion was formed on the radial outside of each reinforcement wire constituting a reinforcement member by extending in the axial direction. The melting point and the viscosity of the material of the inner layer were higher than those of Example 1. Therefore, it was inferred that the length of the protrusion in the axial direction was shorter than that of Example 1.

A catheter main body was produced in the same method as that in Example 1 except that a reinforcement wire was disposed on the outer surface of the inner layer tube without being embedded into the inner layer tube. Accordingly, the catheter main body which has a penetrated lumen and has an outer diameter of 2.06 mm, an inner diameter of 1.80 mm, and an inner/outer diameter ratio of 0.87 was obtained.

A catheter main body was produced in the same method as that in Example 2 except that a reinforcement wire was disposed on the outer surface of the inner layer tube without being embedded into the inner layer tube. Accordingly, the catheter main body which has a penetrated lumen and has an outer diameter of 2.06 mm, an inner diameter of 1.80 mm, and an inner/outer diameter ratio of 0.87 was obtained.

Figure 11:
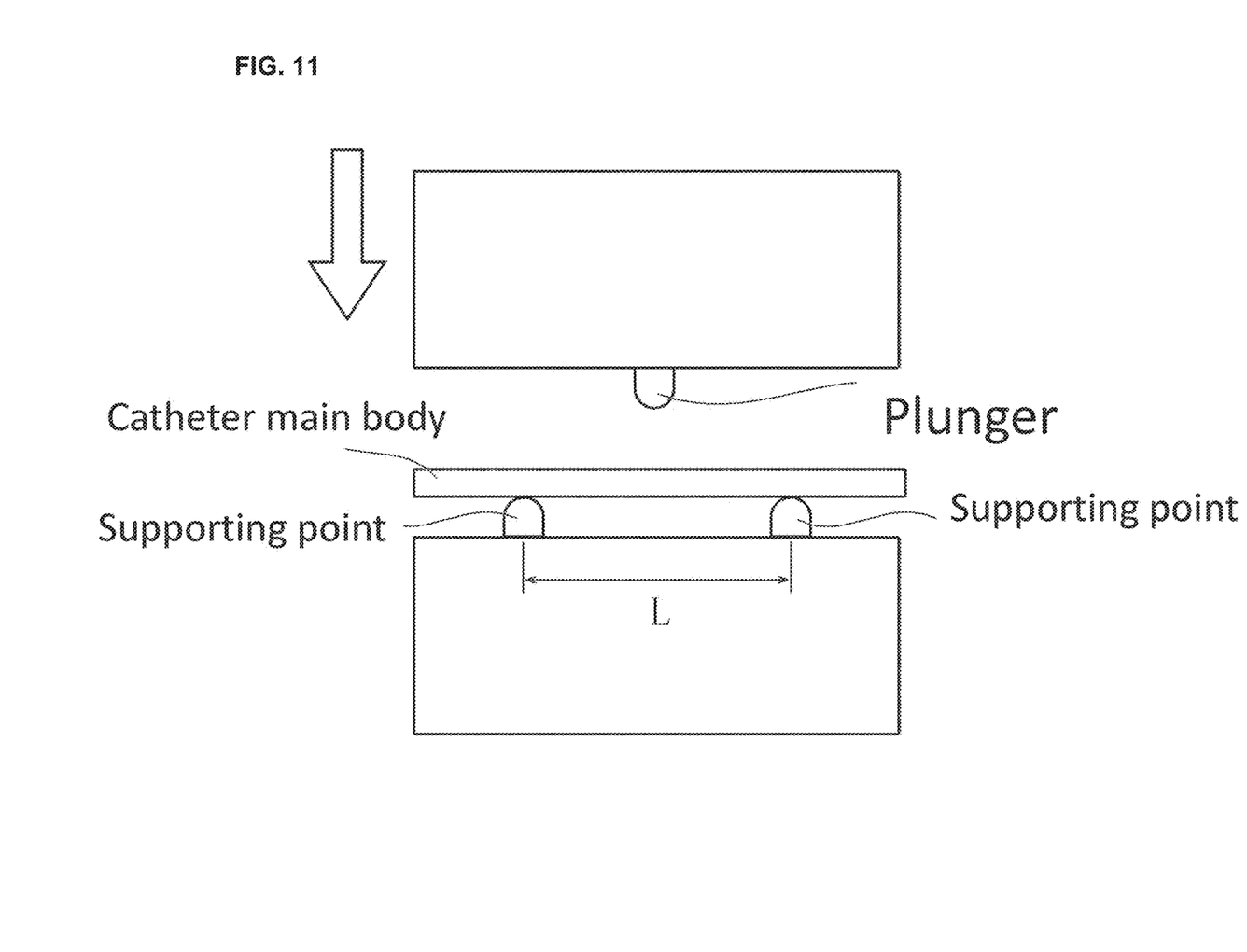
FIG. 11 is a schematic view for illustrating a flexural stress evaluation test.

Flexural stress evaluation tests were performed using the obtained catheter main bodies in the examples and the comparative examples. For the tests, Autograph (AG-X 1 kN manufactured by Shimadzu Corporation) was used (refer to FIG. 11). First, the load capacity of the Autograph was set to 50 N and a plunger (indenter) for 50 N was attached to the Autograph. Next, supporting points on a supporting table were disposed at a distance L=25.4 mm between the supporting points and were positioned such that a distal end of the plunger came into contact with the center of the two supporting points.

Next, the plunger was brought to a catheter main body so as to vertically come into contact with the catheter main body such that the center (20 mm from an end portion) of each of the catheter main bodies (6 Fr: outer diameter of 2.06 mm) in Examples 1 and 2 and Comparative Examples 1 and 2 which were cut to a length of 40 mm in the axial direction came into contact with the distal end of the plunger.

Next, the tests were performed at a test speed of 5 mm/minute, a pushing distance of 10 mm, and at room temperature. The value of the flexural stress measured temporarily increased, and then, decreased in accordance with deformation of a catheter main body. The stress (stress peak value) and the pushing distance (distance during a stress peak) during a peak were recorded from a chart. The results are shown in Table 1.

TABLE 1

|  | Stress peak value (gf) | Distance during stress peak (mm) |
| --- | --- | --- |
| Example 1 | 170 | 4.5 |
| Example 2 | 230 | 4.6 |
| Comparative Example 1 | 155 | 2.1 |
| Comparative Example 2 | 195 | 2.1 |

From Table 1, it was confirmed that the maximum peak values of the stress in Example 1 and Example 2 were higher than those in Comparative Example 1 and Comparative Example 2 and the pushing distances when the stress became the maximum peak in Example 1 and Example 2 were longer than those in Comparative Example 1 and Comparative Example 2. This shows that, in Example 1 and Example 2, with the formation of the protrusion in the inner layer, the bonding joining strength between the inner layer and the outer layer improves, the structure disorder such as separation at an interface between the inner layer and the outer layer or the like hardly occurs, and the physical properties hardly deteriorate.

Note that the present disclosure is not limited only to the above-described embodiment, and various modifications can be made by those skilled in the art within the technical ideas of the present disclosure. For example, the catheter 1 according to the present embodiment is a guiding catheter, but may be a catheter other than the guiding catheter.

In addition, the reinforcement member interposed between the inner layer and the outer layer may not be a reinforcement member which reinforces a catheter with the strength of the reinforcement member itself. In this case, as the reinforcement member, it is possible to use a material which is comparatively softer than the outer layer or the inner layer and is not melted at a temperature when the reinforcement member is covered with the outer layer. By doing this, it is possible to maintain the flexibility in a flexible site in which no reinforcement member with high strength may be provided, and to bond (reinforce) the inner layer and the outer layer with a high bonding strength.

In addition, other layers may be provided on the radial inside of the inner layer and/or on the radial inside of the outer layer. Moreover, even at an interface with the other layers, the structure (structure with protrusions) according to the present disclosure may be formed.

In addition, the reinforcement member may be completely embedded into the inner layer and the outer layer may not come into contact with the reinforcement member. Even with such a configuration, it is possible to achieve an effect in which adhesiveness between the inner layer and the outer layer is increased.

The detailed description above describes a catheter which is inserted into a biological lumen and a method for manufacturing the same. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
    an inner layer as a tube shaped body made of a thermoplastic resin and an outer layer, as a tube shaped body made of a thermoplastic resin, coming into contact with an outer surface of the inner layer;
    a reinforcement member which is at least partially embedded in the inner layer and includes a gap of the reinforcement member leading the inner layer toward a radial outside of the catheter; and
    wherein the inner layer has a protrusion protruding from the gap of the reinforcement member and extending in an axial direction of the catheter and overlapping the reinforcement member while protruding from the gap of the reinforcement member to the radial outside, and
    wherein the protrusion is positioned on the radial outside of the reinforcement member and ingrows into the outer layer.

2. The catheter according to claim 1,
    wherein the protrusion comprises a plurality of the protrusions protruding from different gaps overlap each other in multiple layers toward the radial outside of the reinforcement member while interposing the outer layer.

3. The catheter according to claim 1,
    wherein the reinforcement member is formed of a wire made of resin having a higher melting point than that of the inner layer.

4. The catheter according to claim 1,
    wherein the reinforcement member is formed of metal, which is interposed between the inner layer and the outer layer.

5. The catheter according to claim 1,
    wherein the gap of the reinforcement member comprised a plurality of gaps, the plurality of gaps of the reinforcement member are formed by being divided in a circumferential direction of the inner layer.

6. The catheter according to claim 1,
    wherein the inner layer and the outer layer are formed of a same kind of thermoplastic resins.

7. The catheter according to claim 1, wherein the protrusion is formed in a scale-like shape.

8. The catheter according to claim 1, wherein the catheter has a proximal side and a distal side, and the protrusion extends toward the proximal side.

9. A catheter comprising:
    an inner layer as a tube shaped body made of a thermoplastic resin and an outer layer, as a tube shaped body made of a thermoplastic resin, coming into contact with an outer surface of the inner layer;
    a reinforcement member which is at least partially embedded in the inner layer and includes a plurality of gaps of the reinforcement member leading the inner layer toward a radial outside of the catheter;

the inner layer having a plurality of protrusions protruding from the plurality of gaps of the reinforcement member, each of the plurality of protrusions extending in an axial direction of the catheter and overlapping the reinforcement member while protruding from different gaps of the plurality of gaps of the reinforcement member to the radial outside, and wherein the each of the plurality of protrusions is positioned on the radial outside of the reinforcement member, and ingrows into the outer layer;

wherein the plurality of the protrusions protruding from the different gaps of the plurality of gaps of the reinforcement member overlap each other in multiple layers toward the radial outside of the reinforcement member while interposing the outer layer; and wherein the reinforcement member is formed of a wire made of resin having a higher melting point than that of the inner layer, or of metal which is interposed between the inner layer and the outer layer.

10. The catheter according to claim 9, wherein the plurality of the gaps of the reinforcement member are formed by being divided in a circumferential direction of the inner layer.

11. The catheter according to claim 9, wherein the inner layer and the outer layer are formed of a same kind of thermoplastic resins.

12. The catheter according to claim 9, wherein the plurality of protrusions overlap each other and are arranged in a circumferential direction and the axial direction, and disposed in a scale-like shape.

13. The catheter according to claim 9, wherein the catheter has a proximal side and a distal side, the plurality of protrusions extending toward the proximal side.

14. The catheter according to claim 9, wherein the plurality of protrusions are stacked on each other.

15. The catheter according to claim 14, wherein the plurality of protrusions stacked on each other is four protrusions to five protrusions.

16. A method for manufacturing a catheter, the method comprising:

disposing a reinforcement member having gaps of the reinforcement member on an outer surface of an inner layer tube, the inner layer tube being a tube shaped body made of a thermoplastic resin;

embedding the reinforcement member in the outer surface of the inner layer tube;

forming an intermediate structure by making a material of the inner layer tube protrude radially outward from the gaps of the reinforcement member;

disposing a material for an outer layer of the catheter, on an outer surface of the intermediate structure, the outer layer of the catheter being a tube shaped body made of a thermoplastic resin; and bonding the inner layer tube and the material for the outer layer to each other while fluidizing the inner layer tube and the material for the outer layer in a state in which the inner layer tube and the material for the outer layer have fluidity such that the material of the inner layer tube protruding from the gaps of the reinforcement member extends in an axial direction of the catheter, overlaps the reinforcement member, and ingrows into the material of the outer layer.

17. The method for manufacturing the catheter according to claim 16, further comprising:

forming the inner layer and the outer layer by applying force to the outer surface of the material for the outer layer toward a direction facing the intermediate structure or the axial direction of the intermediate structure in a state in which the inner layer tube and the material for the outer layer have fluidity, and by bonding the inner layer tube and the material for the outer layer to each other while fluidizing the inner layer tube and the material for the outer layer.

18. The method for manufacturing the catheter according to claim 16, further comprising: heating at least one of the inner layer tube and the reinforcement member.

19. The method for manufacturing the catheter according to claim 16, further comprising: heating the inner layer tube.

20. The method for manufacturing the catheter according to claim 16 the fluidities of the material of the inner layer tube and the material for the outer layer are different from each other.

* * * * *